United States Patent [19]

Buckler

[11] Patent Number: 4,486,344

[45] Date of Patent: Dec. 4, 1984

[54] UREA-LINKED IMMUNOGENS, ANTIBODIES, AND PREPARATIVE METHOD

[75] Inventor: Robert T. Buckler, Edwardsburg, Mich.

[73] Assignee: Miles Laboratories, Inc., Elkhart, Ind.

[21] Appl. No.: 479,757

[22] Filed: Mar. 28, 1983

[51] Int. Cl.³ ..................... A61K 37/04; A61K 39/00
[52] U.S. Cl. .............................. 260/121; 260/112 R; 260/112 B; 424/85; 424/88; 424/177
[58] Field of Search ............... 260/112 R, 112 B, 121; 424/16, 36, 85, 88, 101, 177, 359, 78

[56] References Cited

U.S. PATENT DOCUMENTS

| | | | |
|---|---|---|---|
| 4,041,076 | 8/1977 | Avenia et al. | 260/112 R |
| 4,192,799 | 3/1980 | Fitzpatrick | 260/112 R |
| 4,218,436 | 8/1980 | Fitzpatrick | 260/112 R |
| 4,276,206 | 6/1981 | Katz | 260/112 R |

OTHER PUBLICATIONS

Vunakis et al., *Methods in Enzymology*, vol. 70, "Immunochemical Techniques", 1980, Academic Press, New York, pp. 85–103.

*Primary Examiner*—John Kight
*Assistant Examiner*—Nathan M. Nutter
*Attorney, Agent, or Firm*—Andrew L. Klawitter

[57] ABSTRACT

Immunogen conjugates comprising amino-functionalized haptens coupled through a carbonyl bridge to amino groups in immunogenic proteins and polypeptides. The resulting simple urea linkage in the conjugate is hydrophilic and contributes essentially no haptenic determinants. The immunogen is characterized by a high epitopic density. The method involves reaction of the hapten with a carbonyl diimidazole followed by addition of the protein or polypeptide carrier. Protein crosslinking problems common to prior art coupling methods are avoided.

9 Claims, No Drawings

1

UREA-LINKED IMMUNOGENS, ANTIBODIES, AND PREPARATIVE METHOD

BACKGROUND OF THE INVENTION

1. Field of the Invention

This invention relates to a novel technique for preparing immunogen conjugates for use in stimulating production of antibodies against a particular hapten. Novel immunogen conjugates and antibodies prepared against such conjugates are provided. Such antibodies are particularly useful as reagents in immunoassays.

Immunoassays are analytical procedures based on specific recognition of the analyte of interest by an appropriately obtained antibody. Antibodies against antigenic analytes are obtained by injecting the antigen into the bloodstream of an animal such as a rabbit. The antigen is recognized as foreign by the immune system of the animal which is accordingly stimulated to produce antibodies to bind the antigen and neutralize it. Serum from such an animal will, therefore, contain immunolobulin proteins (humoral antibodies) which possess a high binding affinity for the antigen inducing the response [*Ligand Assay*, J. Langan and J. J. Clapp, Eds., Masson Publ. USA, Inc. (New York, 1981), p. 1 et seq]. Substances of relatively low molecular weight, e.g., less than 1500, however, may be only weakly antigenic or unable to stimulate antibody production at all. Nevertheless, antibodies can be raised to such small molecules (referred to as haptens) by immunization with conjugates made up of such low molecular weight substances covalently linked to immunogenic carrier molcules, commonly proteins or polypeptides. The most common protein carriers are the serum albumins of various species, hemocyanin, thyroglobulin and fibrinogen [*Methods in Enzymology*, Vol. 70, H. Van Vunakis and J. J. Langone, Eds., Academic Press (New York, 1980), p 85].

The type of linkage by which the hapten is attached to the carrier is important for optimum antibody production. Coupling the hapten by means of amide linkages to the terminal amino or carboxyl functions of the protein has been reported to give conjugates of high antigenicity, presumably because this mode of coupling locates the haptens on the surface of the macromolecule where they are more accessible to the receptors in the lymphoid cells [N. Hanna et al, *Proc. Soc. Exp. Biol. Med.* 140(1): 89–92 (1972)]. Many reagents adapted from peptide chemistry, including carbonyl diimidazole, have been used to attach carboxyl- or amino-functionalized haptens to proteins. These methods are all based on activating the carboxyl component toward amide bond formation [see *The Peptides*, Vol. I, E. Gross and J. Meienhofer, Eds., Academic Press, New York, 1979, p. 66; and U. Axen, Prostaglandins 5(1): 45-7 (1974)]. Difficulties are encountered, however, when this approach is used to link amino-containing haptens to proteins. Proteins contain both amino and carboxyl groups. Activation of protein carboxyl groups, particularly by carbodiimides, tends to form intra and intermolecular amide bonds and polymerize or crosslink the protein, often forming insoluble complexes [S. Bauminger and M. Wilcheck, *Methods Enzymol.* 70 (Part A): 159 (1980)].

2. Description of the Prior Art

One way reported in the literature to circumvent the crosslinking problem is to attach amino-functionalized haptens to the amino groups of the protein carrier by means of bifunctional reagents which do not activate carboxyl or other functional groups. Many such reagents are known and include toluene-2,4-diisocyanate [C. H. W. Hirs, and S. N. Timasheff, *Methods Enzymol.* 25 (Part B): 625 (1972)]; difluorodinitrobenzene [H. S. Tager, *Anal. Biochem.* 71 (2): 367-75 (1976)]; glutaraldehyde [L. A. Frohman et al, *Endocrinol.* 87: 1055 (1970)]; trichlorotriazine [T. Lang et al, J. C. S. Perkin I: 2889 (1977)]; 4-fluoro-3-nitrophenyl sulfone [P. Cuatrecasas et al, *J. Biol. Chem.* 244: 406 (1969)]; and 2,2'-dicarboxy-4,4'-azophenyldiisothiocyanate [H. Fasold, *Biochem. Z.* 342: 288 (1965)]. The use of such reagents, however, introduces an additional complication. The structural residue contributed by the difunctional linking group introduces another haptenic moiety or antigenic determinant into the immunogen [see M. B. Liu et al, *J. Antibiotics* 34: 898 (1981); *Chem. Abst.* 95: 95251t (1981)]. Where the same linking group is used to prepare a labeled conjugate of the hapten for the immunoassay, recognition of the linking group in addition to the distinguishing features of the hapten itself can result in higher affinity of the resulting antibodies for the labeled derivative than for the free analyte and lead to an immunoassay of diminished sensitivity. The need for an inert or benign bridge therefore exists whenever an external label is used as the marker for immunoassays where high sensitivity is required [J. E. T. Corrie et al, *J. Endocrinol,* 87: 8P (1980)].

The state-of-the-art of preparing antibodies to haptens such as drugs is represented by Weinryb et al, *Drug Metabolism Reviews* 10: 271(1979); Playfair et al, *Br. Med. Bull.* 30: 24(1974); Broughton et al, *Clin. Chem.* 22: 726(1976); and Butler, *J. Immunol. Meth.* 7: 1(1976) and *Pharmacol. Rev.* 29(2): 103(1978).

The coupling of di-, tri-, and tetrapeptides to aminomethylated polymers through various coupling routes, including the use of carbonyl diimidazole, is described by A. Orlowska and S. Drabarek, *Pol. J. Chem.* 54: 2329-36(1980); *Chem. Abst.* 95: 81506f (1981).

SUMMARY OF THE INVENTION

The present invention uniquely provides an immunogen conjugate wherein an amino-functionalized hapten is covalently linked to an immunogenic protein or polypeptide carrier through an essentially inert or benign linkage. The immunogen conjugates are of the formula:

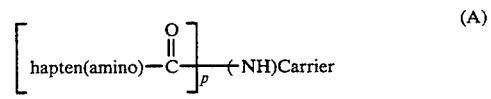

wherein hapten represents the hapten coupled through an amino group, usually a primary amino group, —(NH) Carrier represents the immunogenic protein or polypeptide coupled directly through amino groups thereon, and p is on the average from 1 to the number of available amino groups on the carrier, usually between about 1 and about 50.

The resulting urea linkage between the hapten and the carrier introduces the smallest possible functional group which can be used to link two amino groups, a single carbonyl group. As a consequence, the immunogen conjugates of the present method possess numerous advantages over the prior art conjugates produced using conventional amine-amine bifunctional linking reagents. The urea linkage introduces no charged groups into the macromolecule. It is, furthermore, a hydrophilic functional group and hydrophilic linking arms are known to reduce nonspecific binding effects in similar macromolecular systems [P. O'Carra et al, *FEBS Lett.* 43: 169 (1974)]. Its small size insures that it will contribute essentially no antigenic determinants to the hapten-carrier conjugate. In addition, the urea functional group is a stable linkage and can be formed under conditions which avoid unnecessary denaturation of the carrier or chemical modification of the hapten. It thus represents an ideal inert or benign linkage for attaching haptens to immunogenic carriers.

The present method is generally applicable to the preparation of immunogen conjugates for any desired haptenic analyte. Where the analyte itself comprises an available reactive primary or secondary amine group, it can serve as the hapten coupled to the carrier by the unique urea linkage of the present invention. Alternatively, or where the analyte does not possess an available reactive amine group, an amino-functionalized derivative is first prepared, as is known in the art, and used as the hapten which is coupled to the carrier. The hapten coupled to the carrier according to the present invention will usually have a molecular weight between about 100 and about 1500.

The present immunogen conjugates are generally prepared by first reacting the amino-containing hapten with an equivalent amount of a carbonyl diimidazole, usually unsubstituted 1,1'-carbonyl-diimidazole (1,1'-carbonyl-bis-1H-imidazole), however, other reagents understood in the art to be phosgene equivalents, e.g., alkyl or aryl substituted carbonyl diimidazoles can also be used [*Chem. Abst.* 66P: 379114(1967)], such as 1,1'-carbonyldi-1,2,4-triazole and 1,1'-carbonyldi-1,3,3-benzo-triazole [G. S. Bethell et al, *J. Chromatogr.* 219: 353(1981)]. The resulting intermediate imidazoylurea derivative is normally not isolated but reacted directly with the selected immunogenic protein or polypeptide carrier to yield the immunogen conjugate. Other phosgene equivalents which can function in a similar manner to produce urea-linked immunogens are p-nitrophenyl chloroformate [N. Kornblum and A. Scott, *J. Org. Chem.* 42: 399 (1977)] and 1,1'-disuccinimidyl carbonate [H. Ogura et al, *Tet. Lett.* 4745 (1979)].

DESCRIPTION OF THE PREFERRED EMBODIMENTS

Amino-functionalized Haptens

The present invention applies generally to the preparation of immunogen conjugates for essentially any haptenic substance, and particularly haptenic analytes such as drugs and hormones for which immunoassay procedures are of interest. Such substances which themselves contain available amino groups and therefore can be coupled directly to the carrier in accordance with the present method include thyroxine, liothyronine, sulfamethoxypyridazine, 4-amino antipyrine, and niturprazine. Haptens which do not possess amino groups suitable for coupling by the carbonyldiimidazole method must be chemically transformed so as to introduce such a functionality without altering the distinguishing haptenic determinants. Syntheses of representative examples of amino-functionalized haptens for certain drugs are known in the literature; e.g., phenytoin [R. C. Wong et al, *Clin. Chem.* 25: 686 (1979)]; phenobarbital [L. M. Krausz et al, *Therap. Drug Monitoring* 2: 261 (1980)]; and theophylline [T. M. Li et al, *Clin. Chem.* 27: 22 (1981)]. Other amino-containing haptens can be prepared as follows: Quinidine can be demethylated by the procedure of Small et al, *J. Med. Chem.* 22: 1019 (1979). The resulting desmethyl compound can be alkylated with N-(3-bromopropyl) phthalimide, then treated with hydrazine to give an appropriate amino-derivative. Dibenzazepine is reacted with phosgene to give the chlorocarbonyl derivative which upon treatment with 1,4-diaminobutane leads to a useful amino-derivative. Theophylline is alkylated with N-(3-bromopropyl) phthalimide and the product reacted with hydrazine to give 7-aminopropyltheophylline. Chloramphenicol is catalytically hydrogenated by the procedure of Nielsen et al, *Acta Chem. Scand.* B 29: 662 (1975) to produce an amino-derivative. Estriol is dissolved in tetrahydrofuran and reacted with acrylonitrile and potassium ethoxide to produce the cyanoethyl ketone which is in turn reduced with aluminum hydride to give the 3-aminopropyl ether. 5,5-(p-Methoxyphenylphenyl) hydantoin is alkylated with propiolactone and sodium ethoxide in dimethylformamide to give 3-(2-carboxyethyl)-5,5-(p-methoxyphenylphenyl) hydantoin [Buckler et al, *J. Med. Chem.* 21: 1254 (1978)]. Treatment of this intermediate with sodium azide/sulfuric acid followed by cleavage of the methoxy group with hydrogen bromide gives the 3-(2-aminoethyl) derivative of 5,5-(p-hydroxyphenylphenyl) hydantoin (HPPH), the principal metabolite of phenytoin.

It will be within the skill of the worker in the field to prepare, if necessary, an appropriate amino-derivative of a haptenic substance for which an antibody is to be prepared.

Immunogen Conjugates

The immunogenic carrier material can be selected from any protein or polypeptide conventionally known for this purpose. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. The albumins and globulins of molecular weight between 30,000 and 200,000 are particularly preferred. Synthetic polypeptides may also be used. Further reference for the state-of-the-art concerning conventional immunogenic carrier materials may be had to the following: Parker, *Radioimmunoassay of Biologically Active Compounds*, Prentice-Hall (Englewood Cliffs, N.J. USA, 1976); Butler, *J. Immunol. Meth.* 7: 1-24 (1975); Weinryb and Shroff, *Drug Metab. Rev.* 10: 271-283 (1975); Broughton and Strong, *Clin. Chem.* 22: 726-732 (1976); and Playfair et al, *Br. Med. Bull,* 30: 24-31 (1974).

The epitopic density, or average number of hapten moieties conjugated to the carrier (indicated by the reference letter p in formula A above), is theoretically limited only by the number of available coupling sites on the carrier molecule selected. However, in the usual situation where the carrier is a naturally occurring protein such as albumin, p will be on the average from 1 to about 50, more normally rom 2 to about 20.

Antibodies

Preparation of specific antibodies using the present immunogen conjugates can follow any conventional technique. Numerous texts are available describing the fundamental aspects of inducing antibody formation, for example reference may be made to Parker, *Radioimmunoassay of Biologically Active Compounds*, Prentice-Hall (Englewood Cliffs, N.J. USA, 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps can be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), *Nature* 266: 495 (1977), *Science* 208: 692 (1980), and *Methods in Enzymology* 73 (Part B): 3–46 (1981).

Antibodies obtained according to the present invention can be used in a variety of different manners, however, they are particularly advantageous when used in performing immunoassays. The antibodies are essentially useful in any desirable immunoassay technique, including agglutination techniques, radioimmunoassays, heterogeneous enzyme immunoassays (cf. U.S. Pat. No. 3,654,090), heterogeneous fluorescent immunoassays (cf. U.S. Pat. Nos. 4,201,763; 4,171,311; 4,133,639 and 3,992,631), and homogeneous (separation-free) immunoassays such as fluorescence quenching or enhancement (cf. U.S. Pat. No. 4,160,016), fluorescence polarization (cf. *J. Exp. Med.* 122: 1029 (1965), enzyme substrate-labeled immunoassay (cf. U.S. Pat. No. 4,279,992 and U.K. Pat. Spec. No. 1,552,607), prosthetic group-labeled immunoassay (cf. U.S. Pat. No. 4,238,565), enzyme modulator-labeled immunoassay, e.g., using inhibitor labels (cf. U.S. Pat. Nos. 4,134,792 and 4,273,866), enzyme-labeled immunoassay (cf. U.S. Pat. No. 3,817,837), energy transfer immunoassay (cf. U.S. Pat. No. 3,996,345), and double antibody steric hindrance immunoassay (cf. U.S. Pat. Nos. 3,935,074 and 3,998,943). Homogeneous immunoassays are typically performed by setting up competition between the analyte and the labeled conjugate of the analyte for binding to antibody and are characterized by the fact that the detectable label property is altered when the labeled conjugate is bound by antibody.

The present invention will now be illustrated, but is not intended to be limited, by the following examples:

EXAMPLES

Preparation of Immunogen Conjugate

N-[4-(Phthalimido)butyl]-2-methylsuccinimide

A mixture of 2 grams (g) [14 millimoles (mmol)] of 2-ethyl-2-methylsuccinimide, 2.98 g (10 mmol) of N-(4-bromobutyl) phthalimide, and 1.45 g (10.5 mmol) of potassium carbonate was heated at 65° C. in 25 milliliters (mL) of dimethylformamide (DMF) for 4 hrs. It was cooled and the solvent removed under high vacuum. The residue was dissolved in methylene chloride, the solution dried over anhydrous magnesium sulfate (MgSO$_4$), filtered and evaporated to give a crystalline residue. Recrystallization from ether:hexane gave the captioned bis-imide as a white solid, mp 79°–80° C.

Analysis: Calculated for $C_{10}H_{22}N_2O_4$: C, 66.75; H, 6.45; N, 8,18. Found: C, 66.47; H, 6.64; N, 8.18.

N-(4-Aminobutyl)-2-ethyl-2-methylsuccinimide

A solution was prepared by dissolving 4.95 g (14 mmol) of the bis-imide from above and 0.5 mL (15 mmol) of 85% hydrazine in 50 mL of absolute ethanol. After heating under argon at 70° C. for 3 hr, the reaction was cooled to room temperature and allowed to stand overnight. Solvent was removed and the residue chromatographed on 200 g of silica gel eluting with 60:10:1 (v/v/v) chloroform (CHCl$_3$):methanol:concentrated ammonium hydroxide. Fractions of 17 mL volume were collected. Fractions numbered 65 through 100 were combined, evaporated, and the gummy residue converted to the hydrochloride salt by treatment with hydrochloric acid (HCl) in methanol. Evaporation gave a gum which crystallized on standing. When dry this amounted to 2.3 g of the HCl salt of the captioned amine as a white solid, mp 108°–110° C.

Analysis: Calculated for $C_{11}H_{20}N_2O_2 \cdot HCl$: C, 53.11; H, 8.51; N, 11.26. Found: C, 53.03; H, 8.72; N, 11.17.

Ethosuximide-BSA Conjugate

To a slurry of 92.1 milligrams (mg) of the HCl salt of N-(4-aminobutyl)2-ethyl-2-methylsuccinimide in 0.6 mL of dry DMF at room temperature under argon was added 107 microliters (μL) of triethylamine. The suspension was stirred 15 min; then a solution of 180.2 mg of carbonyldiimidazole (CDI) in 0.6 mL of DMF was added via syringe in one portion. The resulting suspension was stirred at room temperature for 50 min to complete formation of the imidazole. It was then added dropwise, over 8 min, to a stirring solution of 250 mg of Miles Pentex ® crystalline bovine serum albumin (BSA) (Miles Laboratories, Inc., Elkhart, IN, USA) in 108 mL of water at pH 4.5 and 5° C. The pH was maintained at 4.5 during and after the addition by an automatic titrator (HCl). After 18 hrs at pH 4.5 and 5° C., the clear, translucent reaction was adjusted to pH 8 with sodium hydroxide solution, and applied to a 3.0×62 cm column of Sephadex G-25F gel (Pharmacia, Piscataway, NJ, USA) in 50 millimolar (mM) TRIS buffer [tris(hydroxymethyl)aminomethane], pH 8.2. The column was eluted with this buffer at a flow rate of 1 mL/min and 10 mL fractions were collected.

The absorbance at 280 nanometers (nm) wavelength was monitored and fractions 11 through 14, which contained the strongly UV absorbing material, were combined. The pool containing the immunogen was placed in 25.5 mm diameter #1 Spectrapor ® membrane tube (Scientific Products, Chicago, IL USA) which had been washed by boiling in 1 liter (L) of water containing a small amount of ethylenediamine tetraacetic acid (EDTA), followed by water rinsing. The product was dialyzed versus 1.0 L of 50 mM TRIS buffer, pH 8.2., at 5° C. over four days with two changes of dialysate. It was then sterile-filtered into a Nalge ® 0.2 micron (μ) sterile filter (Scientific Products) and stored at 5° C.

A 4-point standard curve was generated for the ratio of light absorption at 420 nanometers (nm) (A$_{420}$) to that at 278 nm ($A_{278}$) versus various ratios of the concentration of the amino-functionalized hapten (supra) to bovine serum albumin (standard error=0.018). The ratios of hapten to BSA were varied between 255 and 0. On this curve, the $A_{240}$: $A_{278}$ ratio indicated an epitope density of 26 for the immunogen conjugate.

The recovery of protein was determined by the absorbance at 280 nm when applied to a five-point curve for $A_{280}$ versus the concentration of bovine serum albumin in 50 mM TRIS buffer, pH 8.2; and was found to be 3.14 μmol (85%).

Preparation of Antibodies

Six milliliters of immunogen (1 mg/mL) was combined with 12 mL of Fruends Complete Adjuvant and 6 mL of saline. Rabbits were immunized simultaneously each with 2 mL of this mixture. Three weeks later they were reimmunized with the same mixture prepared with incomplete Fruends adjuvant. The booster immunizations were repeated every five weeks. Test bleedings were taken one week after the boosters. Antiserum with suitable titers were obtained by four months after the initial immunization.

Preparation of Labeled Conjugate

N-[4-(7-β-Galactosylcoumarin-3-carboxamido)]-2-ethyl-2-methyl-succinimide

A solution of 320 mg (1 mmol) of 7-β-galactosylcoumarin-3-carboxylic acid [J. F. Burd, et al, *Clin. Chem.* 23: 1402 (1977)] and 1 equivalent of triethylamine in 10 mL of dry DMF was cooled in an ice bath while stirring under argon. To this was added dropwise 120 mg (0.92 mmol) of isobutyl chloroformate. Stirring was continued in the cold for 15 minutes to complete the formation of the mixed anhydride. The hydrochloride salt of the aminobutyl-succinimide derivative (supra) (200 mg, 0.8 mmol) and 1 equivalent of triethylamine were dissolved in 3 mL of dry DMF and combined with the mixed anhydride solution. After 1 hour the solvent was evaporated and the residue chromatographed on 70 g of silica gel eluting with 97:3 (v/v) 2-propanol:1M aqueous triethylammonium bicarbonate. Fifteen mL fractions were collected. Fractions 18 through 30 were combined and evaporated to leave a residue which crystallized when treated with ethanol. When dry this amounted to 230 mg of the fluorogenic labeled reagent conjugate as a white powder, mp 162°-163° C.

Immunoassay

A homogeneous substrate-labeled fluorescent immunoassay (SLFIA-U.S. Pat. No. 4,279,992) for ethosuximide was established as follows:

A. Reagents

1. Antibody/Enzyme Reagent-50 mM Bicine buffer [N,N-bis-(2-hydroxyethyl) glycine, Calbiochem-Behring Corp., LaJolla, Calif. USA], pH 8.3, containing 0.1 units/ml β-galactosidase, sufficient antiserum raised against the ethosuximide immunogen to decrease fluorescence to approximately 15% of that in the absence of antiserum, and 15.4 mM sodium azide.

2. Conjugate Reagent—30 mM formate buffer, pH 3.5, containing 0.001% (v/v) Tween 20 detergent (Sigma Chemical Co., St. Louis, MO USA), and 0.13 μM (micromolar) of the labeled conjugate and 15.4 mM sodium azide.

3. Ethosuximide Standards-USP reference standard ethosuximide added to normal human serum; diluted 51 fold with 50 mM Bicine buffer, containing 15.4 mM sodium azide.

B. Assay Method

To 3.1 ml volumes of the Antibody/Enzyme Reagent in cuvettes were added 100 μl of the diluted Ethosuximide Standards. Then to begin the reaction, 100 μl of the Conjugate Reagent was added to each cuvette with mixing. After 20 minutes the fluorescence intensity was measured in each cuvette (excitation 400 nm, emission 450 nm).

C. Results

Performance of the assay yielded the following results:

| Ethosuximide (μg/ml) | Normalized Fluorescence Units |
|---|---|
| 0 | 31.3 |
| 20 | 47.5 |
| 50 | 65.2 |
| 100 | 80.1 |
| 150 | 90.0 |

The immunoassay could be used to determine ethosuximide concentrations in serum samples.

What is claimed is:

1. An immunogen conjugate for use in preparing antibodies against a particular hapten which contains a primary or secondary amine group, which conjugate is of the formula:

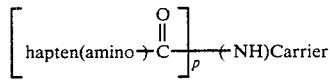

wherein hapten(amino)—represents said hapten coupled through said primary or secondary amine group, —(NH)Carrier represents an immunogenic protein or polypeptide coupled directly through amino groups thereon, whereby said amine-containing hapten is coupled to said Carrier through a urea linkage, and p is on the average from 1 to the number of available amino groups on Carrier.

2. The conjugate of claim 1 wherein p is on the average from 1 to about 50.

3. The conjugate of claim 1 wherein said immunogenic protein or polypeptide is an albumin.

4. The conjugate of claim 1 wherein said hapten has a molecular weight between about 100 and about 1500.

5. An antibody prepared against the immunogen conjugate of claim 1.

6. An antibody prepared against the immunogen conjugate of claim 2.

7. An antibody prepared against the immunogen conjugate of claim 4.

8. A method for preparing an immunogen conjugate according to claim 1, comprising the steps of reacting said hapten with a carbonyl diimidazole and thereafter contacting the resulting activated hapten with said immunogenic protein or polypeptide.

9. The conjugate of claim 1 wherein said hapten contains a primary amine group and wherein said conjugate has the formula:

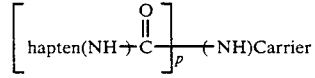

wherein hapten (NH)—represents said hapten coupled through said primary amine group.

* * * * *